United States Patent [19]

Pfizenmaier et al.

[11] Patent Number: 5,736,138
[45] Date of Patent: Apr. 7, 1998

[54] MONOCLONAL ANTIBODIES WITH SPECIFIC BINDING AGAINST MEMBRANE PROTEINS ON HUMAN CELLS, AND PHARMACEUTICAL COMPOSITIONS CONTAINING THEM

[75] Inventors: Klaus Pfizenmaier, Lindenallee 7, D-3400 Göttingen; Peter Scheurich, Uhlandstrasse 18 a, D-3406 Bovenden; Bettina Thoma, Rastenburgerstrasse 13, D-3400 Göttingen, all of Germany

[73] Assignees: Klaus Pfizenmaier; Peter Scheurich; Bettina Thoma, all of, Germany

[21] Appl. No.: 654,257

[22] Filed: Feb. 12, 1991

[30] Foreign Application Priority Data

Feb. 28, 1990 [DE] Germany ............... 40 06 269.5

[51] Int. Cl.⁶ ............... A61K 39/395; A61K 39/00; C07K 16/28; C07K 16/18
[52] U.S. Cl. ............... 424/143.1; 424/133.1; 424/172.1; 424/144.1; 424/152.1; 424/154.1; 424/173.1; 424/809; 435/70.21; 530/399; 530/351; 530/388.22; 530/388.9; 530/388.85; 530/866; 530/387.1; 530/388.73
[58] Field of Search ............... 424/85.1, 85.8, 424/133.1, 143.1, 172.1, 144.1, 152.1, 154.1, 173.1, 809; 435/70.21, 240.27; 530/399, 387, 351, 388.22, 388.9, 388.85, 866, 387.1, 388.73

[56] References Cited

U.S. PATENT DOCUMENTS

4,770,995  9/1988  Rubin et al. ............... 435/7

FOREIGN PATENT DOCUMENTS

0230574  8/1987  European Pat. Off.
0334165  9/1989  European Pat. Off.

OTHER PUBLICATIONS

Harris et al., TIBTECH, 11:42–44, 1993.
Edgington, Bio/Technology 10:383–386, 388, 389, 1992.
Cross et al., Inf. and Imm., 61:2741–47, 1993.
J. Exp. Med., Ban 171, Nr. 2, 1. Feb. 1990, pp. 415–426, The Rockefeller University Press, New York, US.
T. Espevik et al.: "Characterization of binding and biological effects of monoclonal antibodies against a human tumor necrosis factor receptor".
The Journal of Biological Chemistry, Band 265, Nr. 3, 25. Jan. 1990, pp. 1531–1536, The American Society for Biochemistry and Molecular Biology, Inc., Baltimore, US; H. Engelmann et al.: "Two tumor necrosis factor–binding proteins purified from human urine".
The Journal of Biological Chemistry, Band 264, Nr. 25, 5 Sep. 1989, pp. 14927–14934, The American Society for Biochemistry and Molecular Biology, Inc., Baltimore, US; H.P. Hohmann et al: "Two different cell types have different major receptors for human tumor necrosis factor (TNFalpha)".
J. Exp. Med., Band 172, Nr. 4, 1 Oct. 1990, pp. 1019–1023, The Rockefeller University Press, New York, US.
B. Thoma et al.: "Identification of a 60–kD tumor necrosis factor (TNF) receptor as the major signal transducing component in TNF responses".
Adolf et al. J. Imm. Methods, 143:127–136, 1991.

(List continued on next page.)

*Primary Examiner*—Christina Y. Chan
*Attorney, Agent, or Firm*—Weiser & Associates P.C.

[57] ABSTRACT

A monoclonal antibody, or fragments thereof, against human TNF receptor protein which antibody neutralizes the known actions of TNFα and/or TNFβ is disclosed. The antibody may be chimeric or humanized. Furthermore, the present invention provides a process for obtaining the above monoclonal antibody, as well as a pharmaceutical composition containing the above monoclonal antibody and/or the above protein with antibody properties.

6 Claims, 3 Drawing Sheets

OTHER PUBLICATIONS

Pfizenmaier et al., Chapter 28, from: "Tumor Necrosis Factors: The Molecules and Their Emerging Role in Medicine", Ed. B. Beutler, Raven Press, 1992, pp. 439–472.
Natanson et al., Ann. Int. Med., 120:771–783, 1994.
Schreiber et al., PNAS, 78:7535–39, 1981.
Simon et al., J. of Trauma, 25:1156–1162 (1985).
Brockmann et al., Am Rev Respir Dis, 134:885–890, (1986).
Taylor et al., J Clin Invest., 79:918–925 (1987).
Hesse et al., Surg, Gynecol, Obstretics, 166:153 (1988).
Redl et al., J. Inf. Dis., 164:383–8, (1991).
Rhein, Biotechnology News Watch, Oct. 4, 1993, pp. 1,3.
Hinshaw et al., Circ. Shock, 30:279–292 (1990).
Schlag et al., Circ. Shock, 34:311–318 (1991).
Schlag et al., Circ. Shock, 38:253–263 (1992).
Redl et al., Am J. Pathol., 139:461–466 (1991).
Herman et al., J. Lab. Clin. Med., 84:731–739 (1974).
Hinshaw et al., J. Surg. Res., 28:151–170 (1980).
Kosanke et al., Lab. Animal Sci, 32:420 (1982).
Hinshaw et al., J. of Trauma, 23:361–365 (1985).
Shalaby et al., J. Exp. Med., vol. 172, pp. 1517–1520, 1990.
Loetscher et al., J. Biochem. Chem., vol. 286, pp. 20131–20138, 1990.
Pryde, Triton X–114: a detergent that has come in from the cold, TIBS 11, 1986, pp. 160–163.
Waldmann, Monocloonal antibodies in diagnosis and therapy, Science vol. 252, 1991, pp. 1657–1662.

H398 – specific immune preparation of p60

MONOCLONAL ANTIBODIES WITH SPECIFIC BINDING AGAINST MEMBRANE PROTEINS ON HUMAN CELLS, AND PHARMACEUTICAL COMPOSITIONS CONTAINING THEM

The present invention is concerned with monoclonal antibodies against membrane proteins on human cells, with proteins with antibody properties, with processes for the preparation of monoclonal antibodies and with pharmaceutical compositions containing said monoclonal antibodies.

The tumour necrosis factor α (TNFα, cachectin) and the tumour necrosis factor β (TNFβ, lymphotoxin) belong to the cytokine family which is a group of polypeptide mediators which transmit signals from one cell to another. The cytokines participate substantially in the molecular communication basis of inflammatory and immune reactions of the body which forms a complex network of signals which adapt the defense reactions of the body to one another.

The tumour necrosis factor is already produced at a very early point of time of an inflammatory or immune reaction and then, in turn, stimulates the immune cells to form many further polypeptides.

Human TNFα is secreted as a protein with a length of 157 amino acids which contains an N-terminal propeptide sequence of 76 amino acids so that pure TNFα has a relative molecular weight of 17 kD (see Beutler and Cerami, Nature, 320, 585–588/1986). Human TNFβ differs structurally from TNFα by the presence strong glycosilation and the absence of an internal disulphide bridge but possesses a 28% homology on the amino acid plane to TNFα. Although the synthesis of both cytokines takes place on the basis of relatively different stimuli, they possess a strongly agreeing spectrum of biological activities and bind to a common receptor (see Aggarwal et al., Nature, 318, 665–667/1985). The genes coding for TNFα and TNFβ are present in very close proximity on a chromosome not only in the case of humans (see Nedwin et al., Nucleic Acids Res., 13, 6361–6373/1985) but also in the case of mice (see Nedospasov et al., Nucleic Acids Res., 14, 7713–7725/1986).

TNF receptors are found on all somatic cells of the body with the exception of the erythrocytes. The receptor number extends from a few hundred copies on certain cells to more than 20,000 on others. However, in most cases, the number of receptors bears no relationship to the sensitivity of the cells. In some cases, for example in the case of T-lymphocytes, the receptor is not present in resting cells or is present in an inactive form but can be induced by primary activation (see Scheurich et al., J. Immunol., 138, 1786–1790/1987). The receptor has a high affinity for its ligands with a dissociation constant of approximately $1 \times 10^{10} M^{-1}$ (see Scheurich et al., Int. J. Cancer, 38, 127–133/1986). According to gel filtration experiments, the TNF receptor appears to be a complex of several different proteins with a relative molecular weight of about 300 kD (see Smith et al., J. Biol. Chem., 261, 14871–14874/1986). In cells of different origin, the dominating ligand-binding subunit of the receptor appears to have a molecular weight of about 80 to 90 kD, whereas in cells of epithelial origin, a subunit of about 60 kD not cross-reacting therewith is additionally present (see Hohmann et al., J. Biol. Chem., 264, 14927–14934/1989). Therefore, it clearly appears that at least two different types of TNF receptors exist. The precise nature of the signal transmission after binding of TNF to the receptor has hitherto not been clarified but it was found that the response of this signal in different tissues differs very greatly.

An administration of TNF can protect the organism against bacterial infections and against high doses of irradiation. A treatment with TNF can also bring about a dying off of tumours, whereby hemorrhages in the tumours are initiated which subsequently dry out and die. Furthermore, TNF appears to be decisive in the transmission of the reaction of the body to a bacterial infection, for example participating in a fever, and helps the body to overcome the infection. Thus, TNF alone and in combination with Other cytokines possesses a very important therapeutic potential.

On the other hand, TNF can also bring about a series of pathological conditions, for example cachexia, tissue damage, gram-negative septic shock due to bacterial endotoxins and brain inflammation in the case of malaria. Furthermore, a cytotoxic effect of TNF was found in the case of cells which have been infected with HIV (see Matsuyama et al., J. Virol., 63, 2504–2509/1989). It is even found that, on a molar basis, the toxicity of TNF in the case of some types is about 100,000 times greater than that of cyanide (see Beutler and Cerami, Nature, 320, 584–588/1986).

Therefore, the concentration in the organism is clearly decisive for the action of TNF. As in the case of many other factors formed in the body, also in the case of TNF there appears to be a narrow degree between usefulness and damage: an active material can be extremely toxic when it is liberated in large amounts or in the wrong place. This high toxicity of TNF in turn brings with it great problems in the case of a possible use as a therapeutic, for example in the case of tumour diseases. Thus, it is an object of the present invention to provide an agent which, in the case of the presence of unphysiologically high TNF levels in the body, brought about either by an excessive endogenic production of the TNF or by a treatment with TNF, especially when a local use with high doses is necessary, can reduce or overcome the pathological symptoms of TNF, especially the appearance of tissue damage and of shock states.

Thus, according to the present invention, there is provided a monoclonal antibody against a membrane protein on human cells, wherein, in the case of binding to human cells which possess a TNF receptor, it at least substantially neutralizes the known actions of TNFα and/or of TNFβ.

The antibody according to the present invention is directed against a surface protein of the human cells with 60 kD in the case of which it appears to be a component of the TNF receptor complex. Competition studies show that the antibody according to the present invention strongly interferes in different cell lines with the binding of TNF to its receptors (see the following Table 1). Surprisingly, however, by binding of the antibody according to the present invention, in the case of all investigated cell lines of different tissue origin (lymphoid, myeloid, epithelial and fibroblast cells), independently of the extent of the competition with the TNF binding, there is given a complete inhibition of the cellular reaction to TNF. From this finding, it can be assumed that the antibody according to the present invention recognises a receptor protein essential for the signal transmission of very different TNF responses and blocks functionally.

Preferably, an antibody according to the present invention can even completely neutralize the observed cytostatic/cytotoxic action of TNF on human cells in tissue cultures (see Pfizenmaier et al., Blut, 55, 1–10/1987a). The antagonistic effectiveness of the antibody according to the present invention was investigated on three different human cell lines. In all systems, the cytotoxic or cytostatic effect of TNFα was additionally strengthened by the presence of interferon-gamma or of protein synthesis inhibitors, for example cycloheximide, whereby IFN-gamma or protein synthesis inhibitor under the conditions used have themselves alone no influence on the measured cellular reactions. It was ascertained that a binding of the antibody according to the present invention completely neutralizes the cytotoxic/cytostatic action of TNF on all three investigated human cell lines. In a similar way, an antibody according to the present invention also neutralizes the action of TNFβ and of murine TNFα which is just as effective on human cell lines.

Furthermore, an antibody according to the present invention also acts as antagonist of the TNF-induced expression of HLA genes. The TNF-induced modulation of HLA genes was investigated in a human cell line of myeloid origin (K562) and in an epithelial carcinoma cell line (Colo 205). In both systems, there was additionally carried out a co-stimulation of TNFα together with interferon-gamma in order to initiate the particular reaction (see Pfizenmaier et al., J. Immunol., 138, 975–980/1987b). In the presence of an antibody according to the present invention, it can, in the case of both systems, result in the complete inhibition of the TNF action.

Finally, an antibody according to the present invention also acts as antagonist of the immune stimulation brought about by TNF. Thus, the stimulation of the interleukine-2 receptor expression on T-lymphocytes and on so-called natural killer cells (NK cells) (see Scheurich et al., 1987, v. supra) can be completely inhibited by binding of an antibody according to the present invention.

An especially preferred subject of the present invention is a special antibody H398 with the ability completely to neutralise the known TNF actions, it being an immunoglobulin of the isotype IgG2a which is expressed by the hybridoma cell line ECACC 90021617 (or H398.6.1) and which has been deposited according to the Budapest Convention and received Accession Number 90021617.

Furthermore, a subject of the present invention is also a protein with antibody properties which has the same binding specificity as the monoclonal antibody according to the present invention. Especially preferred in this sense is a protein with antibody properties which possesses substantially the same antigen binding positions as the monoclonal antibody H398 according to the present invention.

By the term "proteins with antibody properties" are to be understood antibodies modified by means of recombinant DNA technology. In order at least substantially to neutralize the action of TNF, it is necessary that such modified proteins have the same binding specificity as the monoclonal antibodies according to the present invention, i.e. they must bind to a 60 kD membrane protein on human cells which is a component of the TNF receptor complex, and they must be able at least substantially to neutralize the known actions of TNFα and/or TNFβ in a therapeutically acceptable concentration range. In order to fulfil these criteria, the modified protein with antibody properties must have a substantially equal antigen binding position as the monoclonal antibody according to the present invention. It is known to the expert in the field of immunology that the binding specificity is characterised by quite definite regions of the antibody, namely, the hypervariable regions. Thus, in the case of a change of an antibody according to the present invention for the production of a modified protein with antibody properties, it is important that no modifications take place in the hypervariable regions of the antibody which change the binding specificity. On the other hand, it is possible to change other regions of the antibody (constant region and/or the non-hypervariable parts of the variable region) in order to impart to the modified protein certain desired properties without the binding characteristics of the antibody being substantially changed. Consequently, the present invention also comprises modified proteins, such as antibody partial fragments, for example $F(ab)_2$, single-chained antibodies or chimerized and especially humanized antibodies (replacement of the antibody regions not participating in the binding by sequences of a human antibody). Especially preferred in this sense are proteins with antibody properties which essentially possess the same antibody-binding region as the antibody H398.

The present invention also provides a process for obtaining a monoclonal antibody according to the present invention in which myeloma cells are fused in the usual manner with spleen cells or T-lymphocytes of a mouse which has been previously hyperimmunized with affinity-purified TNF receptor material from human P60 antigen-positive cells, for example HL-60 (ATCC No. CCL 240).

For the purification of the TNF receptor, cell membranes are first prepared, subsequently solubilized and then purified over a TNF affinity column. The preparation of the cell membranes preferably takes place by homogenization in a glass/glass homogenizer in which a pre-treatment in a hypotonic medium can possibly take place. There then follows first a separation of the cell nuclei and of the still intact cells, followed by a pelleting of the cell membranes by centrifuging. According to the present invention, the solubilization of the TNF receptor protein takes place with a buffer which contains a non-ionic detergent, preferably about 1% TRITON X-100. The solubilization buffer can additionally also contain leupeptin, aprotinin and the protease inhibiting material diisopropyl fluorophosphate (DFP). The TNF affinity column is thereby prepared by coupling TNF, preferably recombinant human TNFα, to an appropriate carrier material, preferably AFFIGEL-15. The elution of the bound receptor takes place in the acidic region at pH 3.0. Subsequently, a still further purification step can take place, namely an acetone precipitation. For this purpose, the sample is mixed with about 3 parts of acetone and kept for a sufficient period of time at a sufficiently low temperature, preferably for 14 hours at −80° C. The resultant precipitate, which contains the receptor protein, is centrifuged off and again taken up in an appropriate buffer.

The hyperimmunization of a mouse with the so-obtained receptor material preferably takes place in three steps. In the first step (day 1), 1 μg. of receptor protein is administered intraperitoneally with complete Freund's adjuvant, in the second step (day 40), 1 μg. of receptor protein, mixed with incomplete Freund's adjuvant, is also administered intraperitoneally and, in the third step (day 55), 2 μg. of receptor protein are administered without adjuvant. The removal of the spleen preferably takes place on day 58 under sterile conditions. The production of hybridoma cell lines takes place according to the usual processes. The immunisation of a mouse for the production of a sufficiently high antibody level against the TNF receptor is, however, also possible by other appropriate immunization protocols which are known to the expert.

The fusion of the spleen cells of a mouse hyperimmunized with the TNF receptor protein can take place in the usual way. The resulting hybridoma clones were tested for a modulation of the TNF binding ability to the TNF receptor-positive human leukemia cell line HL-60 (ATCC No. CCL 240).

In this way, from 413 investigated hybridoma clones, a hybridoma cell line could be obtained which secretes an antibody according to the present invention.

The present invention also provides a pharmaceutical composition which contains a monoclonal antibody according to the present invention and/or a protein according to the present invention with antibody properties as active material, optionally together with conventional carrier, adjuvant and/or filling materials.

For the biological action of TNFα and TNFβ, the binding to specific cell membrane receptors with high affinity is a prerequisite (see Pfizenmaier et al., 1987, v. supra). Therefore, the antibody according to the present invention can be used diagnostically in order to detect cellular TNF receptors and in order to identify potentially TNF-reactive cells in various tissues/organs. Furthermore, the above-mentioned antibody can be used for the detection of secreted receptor fragments in serum and in other body fluids.

The greater importance of antibodies according to the present invention lies in their property of at least substantially inhibiting the known biological actions of TNFα and TNFβ. For a TNF-neutralising action in vitro, it is sufficient when the antibody is administered together with the cytokine; a preincubation with anti-receptor antibody is not necessary in vitro.

On the basis of these outstanding antagonistic properties in various in vitro experimental models, such an antibody is of very great potential therapeutic importance. An antibody according to the present invention could find use in the case of all diseases which involve increased pathological TNFα/TNFβ levels in the serum and/or in other body fluids and in the case of which TNFα/TNFβ has been recognized or assumed to be the pathogenic principle (see Old, Nature, 326, 330–331/1987; Warren et al., Mod. Pathol., 1, 242–247/1988; Beutler and Cerami, Ann. Rev. Biochem., 57, 505–518/1989; Grau et al., Immunol. Rev., 112, 49–70/1989). To these belong autoimmune diseases, for example rheumatoid arthritis, and cancerous diseases which are involved with a deregulated TNFα/TNFβ production of the malignant cells themselves, for example myeloma, or of the immune system for example $CD4^+$ cells in the case of chronic B-lymphatic leukemia; B-CLL. In particular, a therapeutic use of an antibody according to the present invention is to be contemplated in the case of TNF-caused, acute, life-endangering courses of diseases, for example in the case of septic shock due to bacterial infections, such as meningococcal sepsis, as well as cerebral malaria. In these cases, it is to be expected that, even after a short-term treatment with the antibodies, the course of the disease can be favorably influenced. However, also in the case of chronic diseases, a therapy with antibodies according to the present invention or with the modified antibodies (for example by exchange of the constant regions of the mouse by constant regions of humans) would be possible.

A further potential field of use of the antibody lies in the co-treatment of AIDS. Since the multiplication of HIV, the cause of AIDS, is stimulated by TNF and is thus regarded as one of the progression factors from the latent to the acute condition of the disease (see Matsuyama et al., J. Virol., 1504–2509/1989), the antibody H398 could be used as antivirally-active principle in the case of those AIDS patients in which either a constitutively increased TNF level has already been ascertained (see Lahdevirta et al., Am. J. Med., 85, 289–291/1989) or in which, by means of exogenic immune-stimulating measures, for example specific active immunization, a TNF production could be induced (see Matsuyama et al., 1989, v. supra). Since the antibody H398 according to the present invention also acts inhibitingly in vitro on the TNF-stimulated activity of the HIV promotor which controls the transcription of the retroviral gene, the use of an antibody according to the present invention could counter a TNF-induced virus transcription and thus a multiplication of infectious viruses.

The dosage of the antibody according to the present invention for the antagonization of undesired side effects of TNF is, of course, also dependent upon the particular case but, especially in the case of an administration of TNF, is preferably from 0.1 to 100 mg. per person.

The following Examples are given for the purpose of illustrating the present invention, reference thereby being made to the accompanying drawings in which.

EXAMPLE 1

Figure 1:
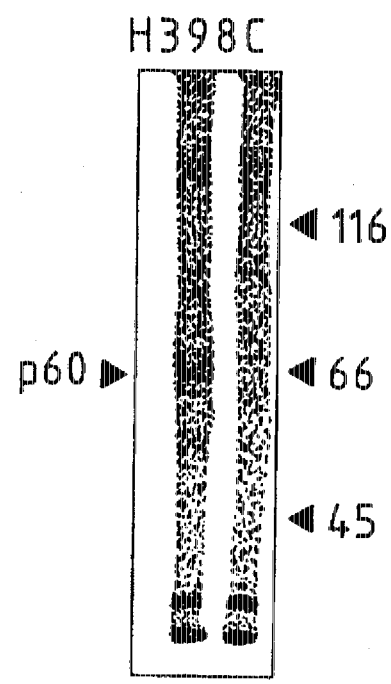
FIG. 1 shows the specific reaction of the antibody H398; it precipitates an iodine-labelled membrane protein with the molecular weight of 60 kDa from HL-60 cells.

Purification of the TNF Receptor Protein 1.1. Preparation of cell membranes

Buffer A:

125 mM sucrose 7.5 mM Tris/HCl, pH 7.4

2 mM EDTA

Buffer B:

100 mM Tris/HCl, pH 7.4

10 mM magnesium chloride 10 mM calcium chloride

2% foetal calf serum (Seramed, Biochrom KG, Berlin)

In each case, on the preparation day, Buffer A and Buffer B were mixed with 1 mM phenylmethylsulphonyl fluoride (PMSF). The freshly harvested cells were, before homogenization in a glass/glass homogenizer, incubated to a cell density of $1 \times 10^8$/ml. in Buffer A for 30 minutes. This pre-treatment in hypotonic medium simplifies the subsequent homogenization with 30 thrusts at 1000 r.p.m. The homogenate was diluted with the same volume of Buffer A and centrifuged at 50 g for 10 minutes in order to separate off nuclei of still intact cells. The sediment was washed once with the same volume of Buffer A and the combined supernatants centrifuged at 12000 g for 30 minutes. The pelleted membranes were subsequently washed twice with Buffer B. All the preparation steps were carried out at 4° C.

1.2. Solubilization of the TNF receptor

Solubilization buffer:

20 mM Tris/HCl, pH 7.4

2 mM magnesium chloride 2 mM calcium chloride

1% TRITON X-100

10 μg./ml. leupeptin

1000 KIU/ml. aprotonin 0.5 μL./ml. DFP

The protease inhibitor DFP (diisopropyl fluorophosphate) (Sigma) was, in each case, added freshly to the buffer. The membrane pellet was suspended in ice-cold solubilization buffer with 1 ml. per $5 \times 10^8$ of cells used and homogenised with 10 thrusts in a glass/glass homogeniser at 1000 r.p.m. After incubation on ice for 1 hour, the batch was centrifuged for 30 minutes at 100,000 g and only the clear supernatant further used.

1.3. Production of the TNF affinity column

For the production of the TNF affinity column, 5 mg. of purified, recombinant human TNFα were coupled to 1 ml. of AFFIGEL 15 according to the instructions of the manufacturer (Biorad). The TNF was previously dialysed for 24 hours in an appropriate dialysis tube against the coupling buffer (0.1M MOPS/HCl, pH 7.5). The AFFIGEL was washed three times with double distilled water and vigorously shaken for 4 hours with the dialysed TNFα solution. The unreacted reactive groups of the AFFIGEL were thereafter saturated for 1 hour by the addition of 1M Tris/HCl (pH 7.4) (end concentration 50 mM). Subsequently, the TNF-Affigel was washed twice with wash buffer (pH 7.4) (see 1.4) and filled into an FPLC column (HR 5/5, Pharmacia, Freiburg). Before the first use of the column, the whole washing and elution program of the affinity purification was carried out once with all of the buffers there used. The whole production of the column was carried out at 4° C. It was also kept at 4° C. in wash buffer (pH 7.4) mixed with 30 mM sodium azide.

1.4. Affinity chromatography

Wash buffer (pH 7.4):

10 mM Tris/HCl, pH 7.4

150 mM sodium chloride 0.1% TRITON X-100

Wash buffer 3D:

10 mM Tris/HCl, pH 7.4

150 mM sodium chloride

10% glycerol

1% sodium desoxycholate 0.1% SDS 0.1% TRITON X-100

Wash buffer (pH 8.6):

10 mM Tris/HCl, pH 8.6

500 mM potassium chloride 0.5% TRITON X-100

Wash buffer (pH 4.5):

50 mM glycine/HCl, pH 4.5

150 mM sodium chloride 0.1% TRITON X-100

Elution buffer (pH 3.0):

150 mM glycine/HCl, pH 3.0

0.1% TRITON X-100

The whole affinity purification of solubilized material was carried out at 4° C. on an HPLC apparatus (Pharmacia, Freiburg). For the sample or buffer application, there was used a superloop of 50 ml. capacity.

The membrane extract of $7 \times 10^{10}$ cells was added with a flow rate of 0.2 ml./minute to the TNF affinity column and subsequently the column was washed with a flow rate of 0.5 ml./minute with the buffers in the following sequence:

1) 10 ml. wash buffer, pH 7.4
2) 10 ml. wash buffer 3D
3) 2 ml. wash buffer, pH 7.4
4) 10 ml. wash buffer, pH 8.6
5) 2 ml. wash buffer, pH 7.4
6) 5 ml. wash buffer, pH 4.5.

The receptor was eluted from the column by means of the acidic elution buffer (pH 3.0) with a rate of flow of 0.1 ml./minute. The eluate was thereby collected in 10 fractions each of 1 ml. and immediately neutralized by means of 200 μl. of a 1M Tris/HCl buffer (pH 7.4) which was placed in the fraction tubes. The fractions were stored at −20° C.

1.5. Precipitation of proteins with acetone

The collected eluate was mixed with acetone at a temperature of −80° C. in the ratio of 1 part of sample/3 parts of acetone and kept for 14 hours at −80° C. After this time, the resultant precipitate was pelleted for 45 minutes at 12000 g in a coolable centrifuge at 0° C. The supernatant was subsequently immediately sucked off and the pellet again dissolved in 400 μl. of 20 mM Tris buffer (pH 7.4) mixed with 0.1% TRITON X-100. TNF binding studies showed that this preparation contained a total of 4 μg. of active receptor protein (total protein content: 80 μg.).

2. Immunization

A 6 week old female mouse of the strain BALB/c was immunised with the receptor material according to the following scheme:

day 1: intraperitoneal injection of 100 μl. receptor preparation (1 μg. receptor protein) mixed with complete Freund's adjuvant (Behringwerk AG, OREC 20/21) (100 μl.);

day 40: intraperitoneal injection of 100 μl. (1 μg. receptor protein) mixed with incomplete Freund's adjuvant (Behringwerk AG, ORED 20/21);

day 55: intraperitoneal injection of 200 μl. (2 μg. receptor protein) without adjuvant day 58: removal of the spleen under sterile conditions, preparation of a spleen cell suspension for the fusion with myeloma cells.

3. Production of hybridomas

The fusion of the spleen cells of a hyperimmunized BALB-C mouse with NSO cells was carried out precisely according to the procedure of Peters et al. (Monoklonale Antikorper, pub. Springer Verlag, Berlin, Heidelberg, 1985) in the ratio of 5:1 and cultured according to standard selection conditions (HAT medium). In all, 413 hybrid clones were isolated and, after transfer to microtitre plates, investigated for reaction with TNF receptor-positive (TNF-R) cells (HL-60).

4. Screening process for the identification of TNF-R-specific, monoclonal antibodies: Modulation of the TNF binding ability $1 \times 10^6$ HL-60 cells were incubated with hybrid culture supernatants (20% end concentration) for 2 hours at 37° C., the supernatant was sucked off after centrifuging and the cells were incubated for a further 60 minutes at 4° C. with radioactive TNF (20 ng./ml.). The specific TNF binding of such cells was compared with that of untreated (NSO supernatants) control cells. Of the 413 investigated clones, one (H398) proved, after double subcloning, to be a stable IgG-producing hybridoma which reproducibly blocked the TNF binding.

5. Immune precipitation of the TNF receptor p60 by means of antibodies H398

$2 \times 10^8$ HL-60 cells/group were superficially iodated according to the lactoperoxidase method, washed and solubilized with TRITON X-100 (1%). After pre-incubation (preclearing) with PROT-A-SEPHAROSE (2 hours at 0° C.), from the TRITON X-100 extract was immune precipitated mAB H398 or IgG control antibody (trace C) coupled with Prot-A-Sepharose (16 hours, 0° C.), the precipitate was washed three times in Tris buffer (20 mM), 0.1% TRITON X-100, 1M sodium chloride (pH 7.8), incubated in SDS sample buffer for 3 minutes at 100° C. and the supernatant separated on a 7.5% PAGE under non-reducing conditions. FIG. 1 of the accompanying drawings shows an autoradiogram after 64 hours exposure of the dried gel. A specific band at 60 kD can only be recognized on the trace of the H398 immune precipitate. After SDS gel electrophoresis, immune-precipitated p60 also possesses specific binding properties in the ligand blot with iodine-labelled TNF.

EXAMPLE 2

Figure 2:
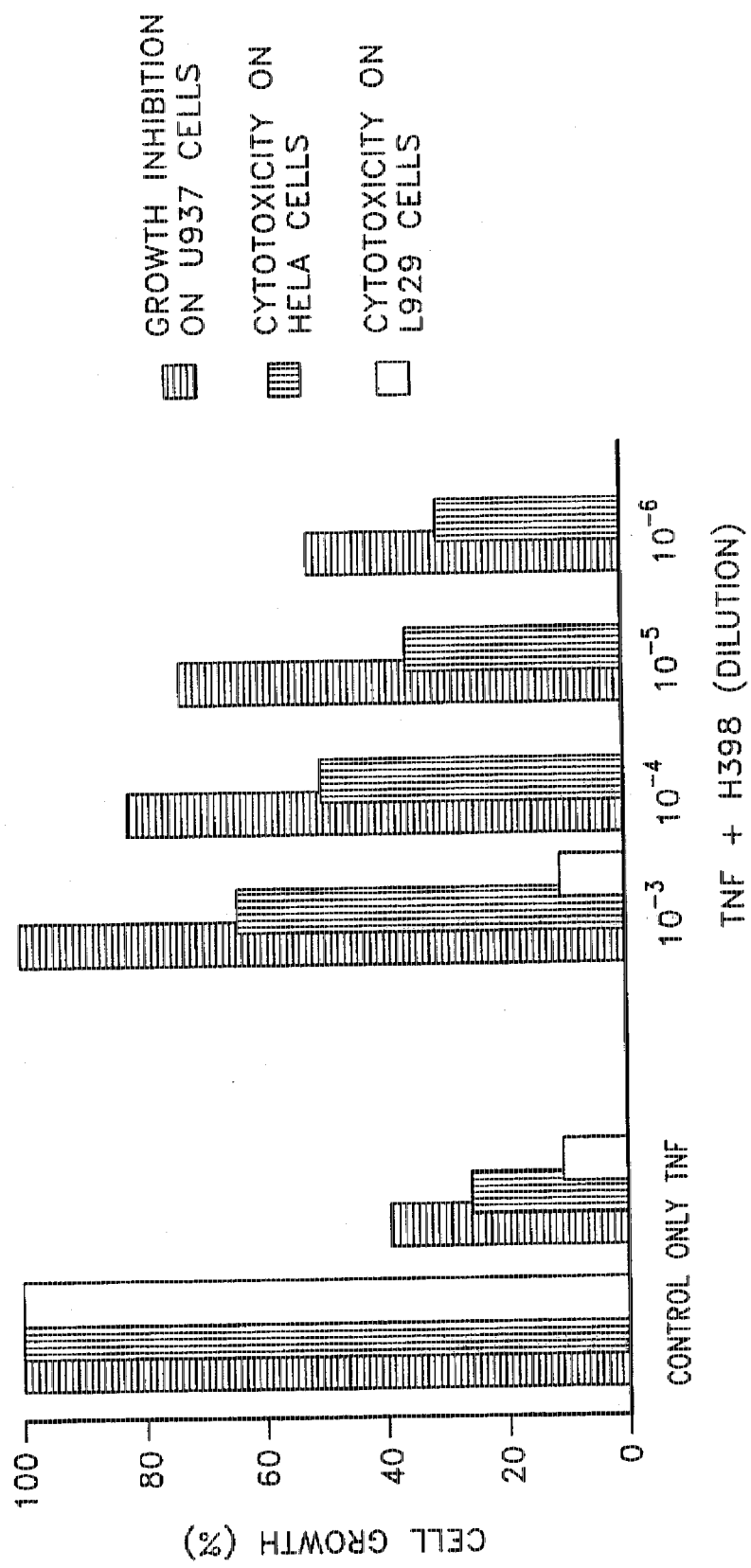
FIG. 2 shows the neutralization of the cytotoxic or cytostatic action brought about by TNF by means of the antibody H398.

Antagonistic action of the antibody H398 on the cytotoxic and cytostatic effect of tumour necrosis factors 1. H398 as TNF antagonist in the case of the cytotoxic action of TNF on HeLa and MCF-7 cells Human HeLa and MCF-7 cells were pre-cultured for 18 hours in microcultures ($3 \times 10^4$ cells in 0.2 ml. culture medium Clicks/RPMI (Cat. No. T125); 5% fetal calf serum (both Seramed, Biochrom, Berlin) and then treated for 7 hours in the presence of 5 µg./ml. cycloheximide with 1 ng./ml. (50 Units) TNF and serial dilutions of H398. Thereafter, the number of surviving cells was quantified by staining with crystal violet. FIG. 2 of the accompanying drawings (grey column) shows that H398 protects HeLa cells against the cytotoxic TNF action dependent upon concentration. Comparable data were obtained with MCF-7 (see the following Table 1):

TABLE 1

Comparison of the ability of H398 to compete with the binding of $^{125}$I-TNF and its antagonistic action in the case of the cellular TNF response

| cell line | competition of the TNF binding % inhibition [1] | antagonistic action % inhibition of the cellular reaction on TNF [2] | test system |
|---|---|---|---|
| U 937 (human) | 50 | 100 | growth inhibition |
| K 562 (human) | 20 | 100 | HLA-A,B,C expression |
| Colo 205 (human) | 20 | 100 | HLA-DR expression |
| HeLa (human) | 88 | >77 [3] | cytotoxicity |
| MCF 7 (human) | 96 | >66 [3] | cytotoxicity |
| YT (human) | 10 | 100 | IL-2 receptor expression |
| L 929 (mouse) | 2 | <5 | cytotoxicity |

[1] There is given the reduction of the specific $^{125}$I-binding (20 ng./ml. $^{125}$I-TNF were mixed with 10 µg./ml. H 398 and incubated with $1 \times 10^6$ cells/batch for 1 hour at 0° C.). The determination of specific TNF binding was carried out as described (see Scheurich et al., 1987).
[2] The given values were achieved with H 398 ascites dilution of $10^{-3}$, corresponding to an antibody concentration of 10 µg./ml.
[3] Because of non-specific toxic side effects of low ascites dilutions ($<10^{-2}$), higher antibody concentrations could not be used here and thus complete inhibition of the TNF response achieved.

2. Blocking of the growth-inhibiting action of TNF on U937 cells

On the human U937 cell line, tumour necrosis factors showed a growth-inhibiting action in synergism with interferon-gamma (Pfizenmaier et al., Blut, 55, 1–10/1978). The cells ($5 \times 10^3$ in 0.2 ml. of culture medium) were cultured for 48 hours in the presence of 10 ng./ml. interferon-gamma, 1 ng./ml. TNF and serial dilutions of H398. The proliferation capacity of the U937 cells was determined by a 6 hour $^3$H-thymidine pulse for 6 hours. In the presence of H398 (10 µg./ml.), it resulted in a complete inhibition of the cytostasis brought about by TNF (see Table 1 and FIG. 2, black column). In a similar way, H398 also protected against TNFβ (lymphotoxin) and also against murine TNF which is also effective on human cells.

3. H398 shows no action on mouse cells

H398 is species-specific and recognizes TNF receptors on human cells but not on mouse cells (cf. also Table 1). FIG. 2 of the accompanying drawings (white columns) shows that H398 on mouse cells possesses no protective action for human TNF. The experimental batch corresponds to the standard test system for the determination of TNF (24 hours culture of murine L929 cells in the presence of 1 µg./ml. actinomycin D, 1 ng./ml. TNF) in the presence and absence of H398 antibody (10 µg./ml.).

EXAMPLE 3

Antagonistic Action of the Antibody H398 on the Expression of HLA Genes Induced by TNF The TNF-induced modulation of HLA genes was investigated in a cell line of myeloid origin (K562) and in an epithelial carcinoma cell line (Colo 205). In both systems, a co-stimulation with interferon-gamma is necessary in order to initiate the reaction in question (see Pfizenmaier et al., J. Immunol., 138, 975–980/1987). In the presence of H398, in both systems there is a complete inhibition of the TNF response (cf. also Table 1).

1. H398 as antagonist of the TNF-strengthened HLA-A,B,C antigen expression on K562

Figure 3:
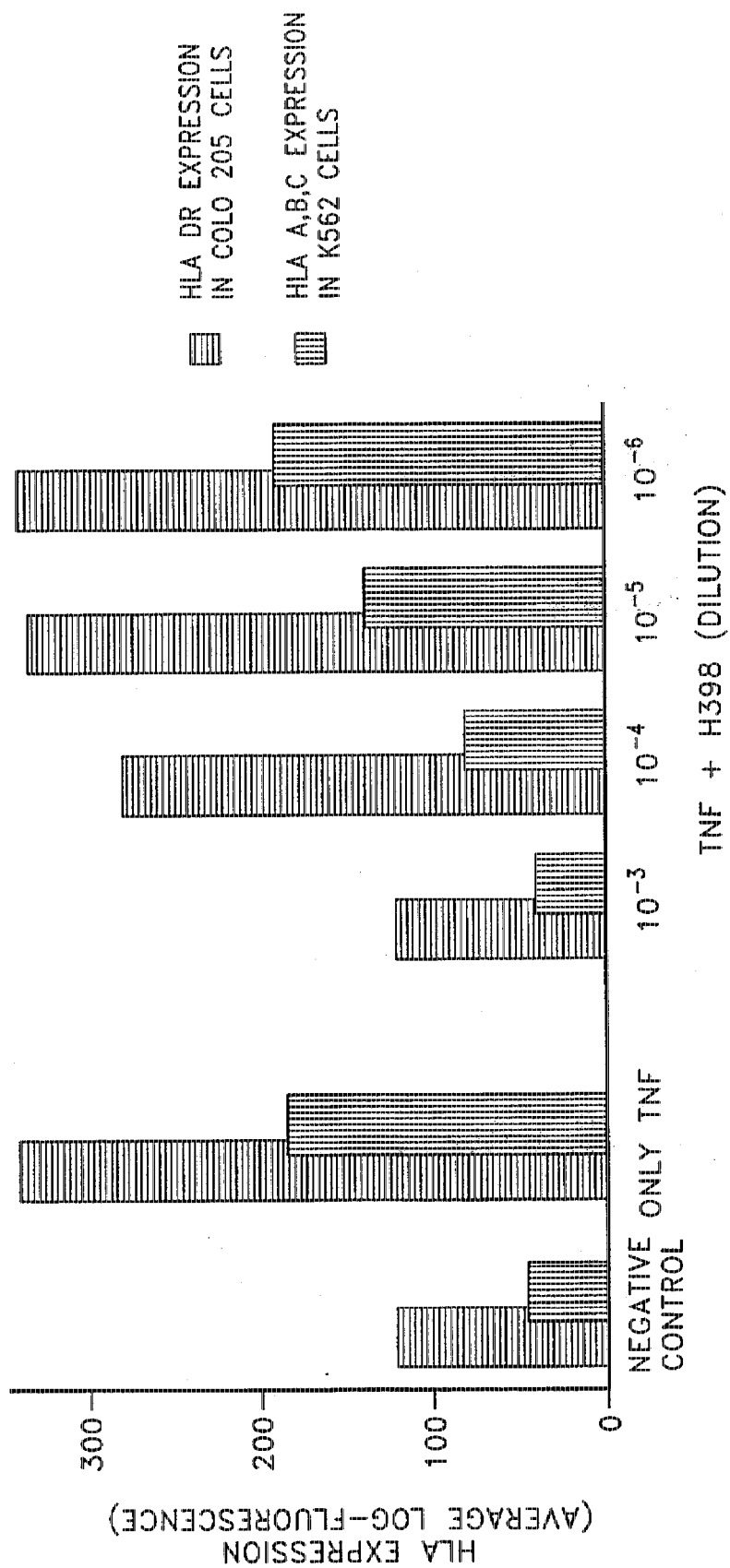
FIG. 3 shows the neutralization of the HLA gene expression induced by TNF by means of the antibody H398.

K562 cells were cultured for 24 hours in the presence of 10 ng./ml. interferon-gamma, 3 ng./ml. TNF and serial dilutions of H398 ($5 \times 10^5$ cells in 2 ml. of culture medium). Thereafter, the cells were harvested and the HLA antigen antigen expression was quantified with the help of HLA-specific monoclonal antibodies by indirect immunofluorescence analysis in a throughflow cytofluorograph. The results are shown in FIG. 3 of the accompanying drawings (grey column) and show that, in the case of 10 µg./ml. H398 ($10^{-3}$ dilution of an ascites with 10 mg./ml. H398 monoclonal antibody), the TNF-induced strengthening of the HLA-A, B,C antigen expression is completely neutralized. A half maximum inhibition is achieved with about 1 µg./ml. of antibody.

2. Antagonistic action of H398 of the TNF-strengthened HLA-DR antigen expression on Colo 205 cells The experimental batch was similar to the one described above (however 48 hours culture period, 0.02 ng./ml. interferon-gamma, 1 ng./ml. TNF). The data in FIG. 3 of the accompanying drawings (black columns) also show a complete removal of the TNF-induced strengthening of HLA-DR gene expression in the case of 10 µg./ml. H398. The half maximum inhibition is here achieved with about 2 µg./ml. H398.

EXAMPLE 4

Antagonistic Action of the Antibody H398 on the Immune Stimulation Brought About by TNF An important immune-regulatory function of TNF is the stimulation of the interleukin-2 receptor expression on T-lymphocytes and on the so-called natural killer cells (NK cells) (see Scheurich et al., J. Immunol., 138, 1786–1790/ 1987). H398 also possesses an antagonistic action in this system. $5\times10^5$ cells of the NK cell line YT in 2 ml. of culture medium were cultured for 24 hours in the presence of 1 and 10 ng./ml. TNF, as well as serial dilutions of H398. The evaluation took place cytofluorographically with the help of anti-interleukin-2 receptor antibodies (anti-Tac). The results illustrated in Table 1 also demonstrate the complete inhibition of this TNF response by H398.

We claim:

1. A monoclonal antibody which has been given accession number H398 at the ECACC, which antibody is a TNF antagonist which binds to the 60-kD component of the human TNF membrane receptor and neutralizes the cytotoxic and cytostatic effects stimulated by TNF, or antigen binding fragments thereof, the 60-kD component being determined by means of 7.5% PAGE under non-reducing conditions.

2. The monoclonal antibody of claim 1 wherein the TNF is TNF-α or TNF-β.

3. The monoclonal antibody of claim 1 wherein the effect neutralized is the expression of HLA genes.

4. The monoclonal antibody of claim 1 wherein the effect neutralized is the immune stimulation of T-lymphocytes and natural killer cells brought about by TNF.

5. A pharmaceutical composition which comprises a monoclonal antibody which has been given accession number H398 at the ECACC, or antigen binding fragments thereof, which antibody is a TNF antagonist which binds to the 60-kD component of the human TNF membrane receptor and neutralizes the cytotoxic and cytostatic effects stimulated by TNF and a pharmaceutically acceptable carrier, the 60-kD component being determined by means of 7.5% PAGE under non-reducing conditions.

6. The pharmaceutical composition of claim 5 wherein the antibody is in a dosage of 0.1 to 100 mg per person.

* * * * *